(12) United States Patent
Barathur et al.

(10) Patent No.: US 9,084,818 B2
(45) Date of Patent: Jul. 21, 2015

(54) TOPICAL DERMAL DELIVERY COMPOSITIONS USING SELF ASSEMBLING NANOPARTICLES WITH CETYLATED COMPONENTS

(71) Applicant: CYMBIOTICS, INC., Escondido, CA (US)

(72) Inventors: Raj R. Barathur, Escondido, CA (US); Jack Bain Bookout, San Diego, CA (US)

(73) Assignee: Cymbiotics, Inc., Escondido, CA (US)

( * ) Notice: Subject to any disclaimer, the term of this patent is extended or adjusted under 35 U.S.C. 154(b) by 0 days.

(21) Appl. No.: 13/767,886

(22) Filed: Feb. 15, 2013

(65) Prior Publication Data

US 2014/0234428 A1     Aug. 21, 2014

(51) Int. Cl.
| A61K 47/14 | (2006.01) |
| A61K 47/10 | (2006.01) |
| A61K 9/00 | (2006.01) |
| A61K 9/107 | (2006.01) |
| A61K 9/127 | (2006.01) |

(52) U.S. Cl.
CPC ............... *A61K 47/14* (2013.01); *A61K 9/0014* (2013.01); *A61K 9/1075* (2013.01); *A61K 9/1272* (2013.01); *A61K 47/10* (2013.01)

(58) Field of Classification Search
CPC . A61K 9/1272; A61K 9/0014; A61K 9/1075; A61K 47/14; A61K 47/10
See application file for complete search history.

(56) References Cited

PUBLICATIONS

Sarpotdar et al., "Pecutaneous Absorption Enhancement by Nonionic Surfactants", Drug Development and Industrial Pharmacy, (1986), vol. 12, pp. 1625-1647.*

* cited by examiner

*Primary Examiner* — Abigail Fisher
*Assistant Examiner* — Daniel L Branson
(74) *Attorney, Agent, or Firm* — MU Patents; Timothy Marc Shropshire (57) ABSTRACT

The invention, a transdermal delivery method, relates to penetration-enhancing pharmaceutical compositions comprising a novel, stable mixture of cetylated esters, cetyl or stearyl alcohols, polar solvents and surfactants, which, under appropriate conditions, combine into amphiphilic nanoparticles within a stabilized liquid dispersion for use in delivery of medicinal agents through the skin. The term cetosomes is used to describe these particles in order to differentiate them from other nanoparticles, such as niosomes, cerasomes, polymeric micelles, dendrimers, liposomes, lipoids, solid lipid nanoparticles and other particles. The self-assembling cetosomes, with both ionic and nonionic points of attraction, incorporate and concentrate a variety of different bioactive agents of interest and demonstrate stable properties with similarities to colloidal molecular structures. The compositions enhance topical transdermal fluxes of bioactives without permanently disrupting natural skin barrier function.

17 Claims, 3 Drawing Sheets

FIGURE 1

Figure 2:
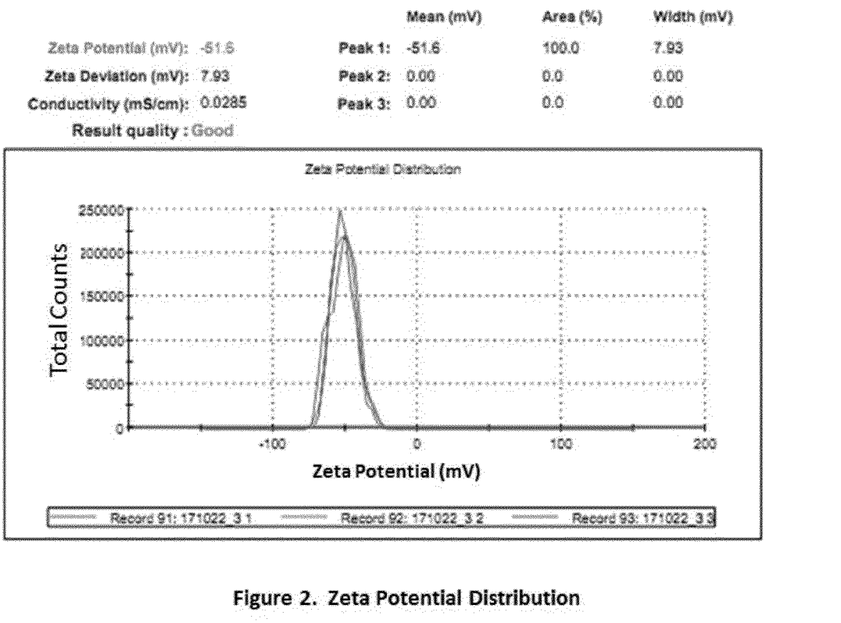

Figure 2. Zeta Potential Distribution

Figure 3:
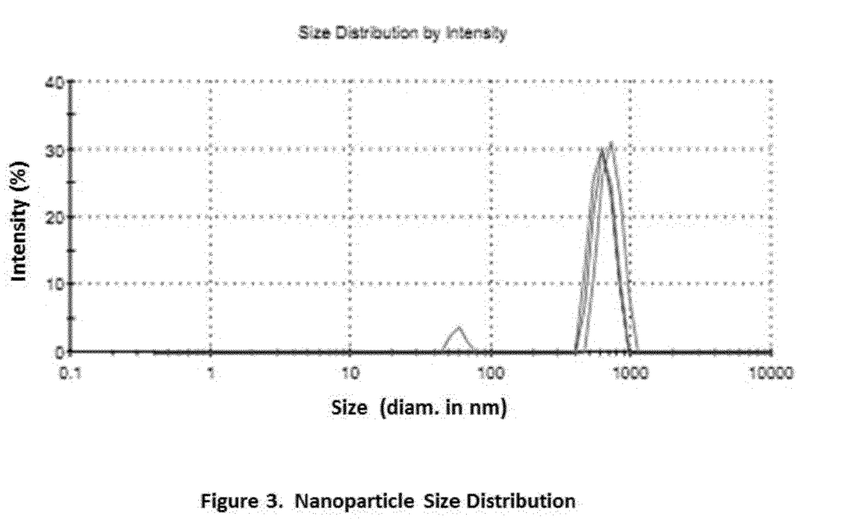

Figure 3. Nanoparticle Size Distribution

US 9,084,818 B2

TOPICAL DERMAL DELIVERY COMPOSITIONS USING SELF ASSEMBLING NANOPARTICLES WITH CETYLATED COMPONENTS

CROSS-REFERENCE TO RELATED APPLICATIONS

The following application is related to the contents presented in this application: U.S. patent application Ser. No. 12,608,963, Barathur and Bookout, submitted Oct. 29, 2009.

STATEMENT REGARDING FEDERALLY SPONSORED RESEARCH OR DEVELOPMENT

Not applicable

BACKGROUND OF INVENTION

1. Description of Related Arts

Many new bioactive pharmaceutical compounds have solubility properties that can adversely affect drug bioavailability and efficacy. These compounds frequently lack either sufficient lipophilicity, reduced transdermal transport, or require some form of protective delivery matrix in order to improve performance. To address these issues many advanced delivery systems have been developed to improve solubility and enhance absorption. As a result, a panorama of such advanced delivery systems have evolved, and these approaches include cerasomes, dendrimers, liposomes, lipoids, micelles, nisosomes and polymeric micelles (US patent application 2012/0116064 by Dai, Liang and Yue; U.S. Pat. No. 6,579,906 to Cooper and Chen, issued Jun. 17, 2003; European Patent EP 0036277 to Papahadjopoulos, issued Aug. 28, 1985; U.S. Pat. No. 5,565,213 to Nakamori, Yoshida, et al., issued Oct. 15, 1996; U.S. Pat. No. 4,694,064 to Tomalia and Kirdhhoff, issued Sep. 15, 1987; U.S. Pat. No. 4,830,857 to Handjani, Ribier, et al., issued May 16, 1989). A review of many of these delivery mechanisms is given in Huynh, et al. Nanomedicine: Nanotechnol Biol and Med, 8, pp. 20-36 (2012), which is incorporated herein for reference.

Many systems derive enhanced attributes through the generation of colloid suspensions with suspended particulates having characteristic dimensions between 1 and 1,000 nm. Some examples of colloidal systems are emulsions, liposomes, microemulsions, multiple and multilayer emulsions, nanocrystal suspensions, solid lipid nanoparticles and polymeric particles [Madene A, Jacquot M, et al., Int J Food Sci Technol, 41, pp. 1-21 (2006); McClements D J, Adv Coll Interface Sci, 174, pp. 1-30 (2012); McClements D J, Decker E A, Weiss J, J Food Sci, 72, pp. R109-24 (2007); Muller R H, Gohla S, Keck C M, Eur J Pharm Biopharm, 78, pp. 1-9 (2011)]. However, transdermal delivery efficiency of many of these platforms (such as solid lipid nanoparticles) is reduced by the particle size achieved, which is often over 100 nm in diameter.

2. Background of the Invention

A key feature of many systems is the use of amphiphilic/semi-polar substances that exhibit both hydrophilic head groups and hydrophobic chain regions. In an aqueous environment, micelle particulates form from these amphiphilic substances with the polar regions facing out, interacting electrostatically with the aqueous phase, and the more hydrophobic regions, consisting of the hydrocarbon chains, facing inward. Such conditions are conducive for entrapment of hydrophobic bioactives within the hydrophobic matrix of the particulate structure. In environments where the oil phase is predominant, amphiphilic components reconform with hydrophobic regions external and hydrophilic regions being internalized.

And depending on the composition of the amphiphilic substances, packing of these molecules can be adjusted to form close packing to that of a looser configuration. In essence the behavior of such particulates can be polyphasic, having different phase configurations based the micelle concentration, composition of the liquid environment and amphiphilic components and temperature. Corkill and Goodman, Adv Colloid Interface Sci, 2, pp. 298-330 (1969) demonstrated that in aqueous solutions containing ampholytic components, the length of the alkyl chain greatly affected the concentration at which micelle formation occurred and the type and number of distinct morphic phases that might occur. The effect of increasing the molecular polarity was found to increase the temperatures necessary for different polymorphic phases to occur. Theoretical models have been developed that reflect the micellar structural phases observed and analyzed using low-angle X-ray diffraction [Lipinski, et al. Adv Drug Deliv Rev, 46, pp. 3-26 (2001); Jorgensen and Duffy, Adv Drug Del Rev, 54, pp. 355-366 (2002); Mannhold and Rekker, Perspect Drug Rev, 18, pp. 1-18 (2000)]. The complexity of conditions necessary to favor different phase formations and then to maintain a stable phase can present challenges to manufacture. The following examples are given to show the concerns with some new delivery systems that should be considered in the use and manufacture of such systems for drug delivery.

Liposomes, manufactured as vesicles of phospholipid bilayers encapsulating an aqueous space (0.03-10 μm diameter) have shown utility of use with a wide variety of drugs. However, hydrolysis or oxidation can degrade the liposomal integrity [Hunt and Tsang, Int J Pharm, 8, pp. 101-110 (1981)] and stability can be compromised due to aggregation, sedimentation of liposome fusion during storage [Wong and Thompson, Biochemistry, 21, pp. 4133-4139 (1982)]. Cerasomes demonstrate improvements over liposomes in regards to high stability towards surfactant solubilization, long term storage and acid treatment [Cao et al., Chem Commun, 46, pp. 5266-5267 (2010)]

Niosomes are non-ionic surfactants based multilamellar or unilamellar vesicles in which an aqueous solution of solute(s) is enclosed by a membrane resulted from the organization of surfactant macro-molecule as bilayer. Like liposomes, niosomes are also characterized by problems limiting shelf life due physical stability affected by aggregation, fusion and leaking [Hu and Rhodes, Int J Pharm, 206, pp. 110-122 (2000)].

Dendrimers also demonstrate potential for use with a wide range of different drug types. However, the system also demonstrates drawbacks in the complexity of dendrimer branch synthesis, the presence of branch defects and difficulties in purification after synthesis [Moses and Moorhouse, Chem Soc Rev, 36, pp. 1249-1262 (2007); Crooks, et al. Topics in Cur Chem, 212, pp. 81-135 (2001)].

Polymeric micelles are nanoscopic core/shell structures formed by amphiphilic block copolymers. They have good stability and good delivery transdermally. Polymers, however, are inherently heterogeneous and can be associated with changes in toxicity and drug efficacy [Duncan, Nature Reviews, 2, pp. 347-360 (2003)].

For transdermal delivery to be effective, system efficacy often requires enhancement through the use of penetration enhancers. The teachings from several patents support the premise that most pharmaceutically active substances can be introduced transdermally or intradermally with the use of penetration enhancers [U.S. Pat. No. 4,913,905 to Frankhauser issued April 1990; U.S. Pat. No. 4,917,676 to Heiber, issued April 1990; U.S. Pat. No. 5,032,403 to Sinnreich, issued July 1991]. Other enhancing components often include the addition of surfactants or chemical ingredients that modify skin barrier properties to increase transdermal flux. The relationship of such components and utilizations will be discussed in relation to this invention.

BRIEF SUMMARY OF INVENTION

The invention is based on the discovery of a unique delivery system, which self assembles and is stable once manufactured. The teachings found in U.S. patent application Ser. No. 12,608,963, Barathur and Bookout, submitted Oct. 29, 2009 are incorporated herein, which describe several combinations of cetylated fatty esters and their functions as amphiphilic penetration enhancers. It was initially found that, when combined with polar solvents, certain combinations of cetylated esters with different alkane chain lengths and polar regions could be used to facilitate the transdermal flux of bioactives with properties that affected the efficacy of delivery through the stratum corneum.

This invention disclosure brings forward the utilization of these cetyl esters in combination with cetylated alcohols, polar solvents and surfactants to form unique nanoparticles or vesicles when suspended within an aqueous media. The particles are characterized by micelle and colloid properties with single particle size ranging from 50 to 850 nm. Because their composition is primarily of cetylated monomers, the particles have been given the designation of term "cetosomes". This helps differentiate these particles from uniquely different particles like niosomes, cerasomes, polymeric micelles, dendrimers, liposomes, lipoids, solid lipid nanoparticles and other particles. The definition of cetosome will be described in detail herein.

By process used and by liquid environment provided, the cetosomes can self-assemble. Cetosomes are generated through phased assemblies as hydrophobic alignments of hydrocarbon chains with polar regions facing out into the aqueous interphase. Interspersed within these vesicular formations and generating an outer corona or mantle region around the core are the polar solvent and solubilizer molecules, which enhance the electrostatic stability with water molecules at the exterior region of the cetosomes. In addition, they also may be incorporated to some degree within the core matrix, which allow for the entry and additional capture of both polar and other hydrophobic bioactive molecules. Cetyl and stearyl alcohols, as defined molar components of the cetosomal matrix, further contribute to the amphiphilic characteristics of the particles and serve as stabilizing components for structural stability. The vesicles are elastic and deformable, yet steric effects favor spherical symmetry. The elasticity is enhanced with edge activators such as surfactants. Surfactants also play a key role in reducing the size of these nanoparticles. They help in the formation of oriented monolayers at interfaces, decrease the size range of the cetosomes, while increasing stability, and provide critical rheological properties to the system.

A key utilization for this invention was that the cetylated fatty esters, cetyl alcohol and stearyl alcohol have melting points well above product utilization temperatures (i.e., they display a thermal phasic nature which can be exploited for this invention). These molecules when heated in an aqueous environment recombine upon cooling into large globular, waxy masses that cannot serve as penetration agents in this physical state. However, temperature elevation allows for component melting, after which other solubilizing and stabilizing components indicated above can be introduced so that as the temperature is reduced and under appropriate emulsifying conditions a coalescing occurs into uniform microparticles with stable colloid properties, and by this manner macro-solidification is eliminated. Where a more hydrophobic interior core within the cetosome is desired, oils or a relatively nonpolar ingredient can be introduced around which the cetosomes form. Under these conditions, particle size tends to become biphasic with a smaller component (cetosomes with "empty", possibly more solid core centers) and larger cetosome particles having larger centers containing (with formulation) oil or nonpolar additive. The smaller component is calculated to have a core formed by a minimal number of amphiphilic layers. The larger cetosome centers can be made with increased capacity for hydrophilic drugs through the use of oils containing mixtures of glyceryl polyethylene glycol oxystearate, fatty acid glyceryl polyglyceryl esters and glyceryl ethoxylate. The larger cetosomes demonstrate birefringent characteristics. This feature has the characteristics of liquid crystallization and does not have the properties of solid crystal formation. Particle birefringence is often the result of light bending effects caused by a lamellar internal structure.

Stability of these cetosomes is due in part to the relatively elevated negative zeta potential (Zp). Factors that contribute to stability include electrostatic interactions between charged groups and oppositely charged groups of surfactants, hydrophobic interactions between the cetosomal agents and the hydrophobic regions of the solvents and surfactants and hydrogen bonding interactions (van der Waals). Stability of the nanoparticles is defined by lack of discernible coalescence or flocculation for periods of 1 month or more after manufacture. The major forms of cetosomes are spherical; however, more complex phase changes can be elicited through modifying composition. The invention has been found to be most efficient for transdermal delivery when the cetosomes are generated in the compact, spherical form.

Compared with other transdermal delivery systems, the formulations containing cetosomes appear to have increased entrapment capacity and greater surface activity for skin penetration. The cetosomes can serve as drug carriers for a wide range of small molecules, peptides and proteins. The combination of cetosomes within the vehicle delivery system has a distinctive effect on the dermal and transdermal delivery of active ingredients. Due to the complexity of the delivery system, some effects contributing to penetration efficiency are not fully defined. Our system is proposed to provide a maximizing of thermodynamic activity for the permeant while incorporating penetration enhancers that increase diffusivity across the skin. For purpose of this submission, a permeant is defined as a molecular species moving through of moving into the tissue. By definition, a penetrant is a molecular species that facilitates in some manner transdermal penetration of the permeant.

Cetosomes tend to facilitate penetration through the stratum corneum and underlying viable skin but may tend not to remain intact during the process, releasing into smaller penetration units containing any carried molecules and thereby initiating the process of penetration. The cetylated esters tend to partition in high concentrations on the skin, which provides an increased diffusion rate for drugs of interest. All cetylated fatty esters by definition contain the cetyl alkane chain. In addition to this alkane with its hydrophobic properties, the fatty acid component of these molecules provides further hydrophobicity but also hydrophilic polar components. Fatty acids with no unsaturated alkane regions provide secondary structure that is straight and that can readily intercalate between membrane lipids with least disruption. Fatty acids with double bonding between carbons in a cis-configuration introduce bending in the secondary structure that when intercalated in the membrane lipids, causes greater disruptions in the membrane configuration. These molecules intercalate within the lipid bilayers with several disruptions—rotating, vibrating, translocating, forming microcavities and increasing the free volume available for drug diffusion. Pooling may occur with permeable pores forming which, for polar molecules, provide greater access to viable epidermis. This may be a critical step in allowing diffusion through the gel-like viscosity of the lipid matrix.

Upon application of vehicle containing the cetosomes to the skin, the fluid phase is drawn by diffusion into the stratum corneum and allows the cetosomes to coalese into larger, fragmenting complexes that concentrate the permeants with the penetration enhancers. The polar solvent and cetylated molecules act in conjunction to allow for rapid absorption and avoid the formation of a waxy film that would slow permeant migration. The primary delivery effect of the cetosome is to move the permeant through the permeation barrier of the stratum corneum to the site desired for utilization of the drug. The structure of the cetylated molecules plays a major role in this permeability process by disrupting the lipid organization of the stratum corneum, increasing the diffusion coefficients of the permeants. Premature drug release is prevented in part through affinities between the drug and core components of the cetosomes, the latter acting as penetrant carriers for controlled release within the dermis and stratum corneum.

Another critical aspect of this invention is the introduction of functional groups within the cetosome that have heightened affinities for the permeants of interest (i.e., functional groups with polar affinities for more ionic permeants such as diclofenac or with more lipophillic affinities for more non-polar permeants). This is accomplished through the selection of the components for the cetosome assembly and the molar ratio of the components added.

1. Hydrophilic compounds and ionized species (log $P_{octanol/water} \leq 3$) require different approaches to penetration than that of more lipophilic chemicals. From the aqueous matrix, these are incorporated within the cetosomes through entrapment during assembly or through introduction of cetylated esters into the cetosome with noncovalent, charged affinities for the drug compound. Additional drug molecules may become associated with the charged corona region around the cetosome. Khalil, Najjar and Sallam, Drug Devel Indust Pharm, 26(4), 375-381 (2000) teach, for example, that different salts of diclofenac exhibit different affinities in relation to micellar positioning. Diclofenac sodium, having greater ionization capacity than diclofenac diethylamine, has a higher potential to be associated with the solvent mantle of micelles, while the latter drug salt has greater affinity for location within the micelle core. Physical properties of the cetosomes appear to establish similar relationships dependent upon the properties of the drug of interest. The cetosomes, however, unlike the micelle, can be compositionally modified to increase core affinity for a drug of interest and still maintain architectural integrity.
2. Lipophilic compounds (log $P_{octanol/water} \geq 3$) have natural affinities for incorporation within the cetosome core, creating a hydrophobic microenvironment within an aqueous medium. This is responsible for encapsulating hydrophobic "guests" and making of the aggregates. Upon skin application, the cetylated molecules in the cetosomes provide more efficient penetration through their affinity for the permeant, complexing as previously noted, and partitioning into the bilayer lipids, disrupting the organized packing but also dispersing within the intercellular lipids to facilitate permeant diffusion.

Upon application to the skin, cetylated components and other penetrant agents allow for enhanced diffusion of the permeant to proceed at rates which are mediated by the properties of the drug molecules and the composition of the cetosome complex. The composition of the cetosomes also helps to reduce water loss from the stratum corneum, increasing hydration and assisting in diffusion of more ionic permeants.

BRIEF DESCRIPTION OF THE DRAWINGS

FIG. 1 shows a concept schematic of a representative nanoparticle of the invention; a center-filled region [5], encapsulated by a core [11] composed of primarily of cetyl esters, cetyl alcohols, stearyl alcohols and surfactant molecules (structures with a terminal "S"); a corona/mantle region [20] contains both surfactant molecules and polar solvent molecules (PS); drug of interest (designated as D).

FIG. 2 shows the zeta potential for the dispersion in composition CLDC0704 as described in Example 1.

FIG. 3 shows the particle distribution sizes for the dispersion particles formed in composition CLDC0704 as described in Example 1.

DETAILED DESCRIPTION OF THE INVENTION

The present invention provides an improved topical delivery system formulated to deliver medicinal substances into or through human or animal skin without permanently disrupting the stratum corneum's natural barrier function. The mechanism of delivery is based on formulations containing novel nanoparticles within which medicinal substances are packaged and delivered transdermally when applied to skin. Four areas pertaining to this invention are described in this section, namely: 1) Properties of cetosomes and the aqueous delivery matrix, 2) Architecture of cetosomes and the transdermal delivery system, 3) Methods for the manufacture of compositions comprising cetosomes and 4) Applications for the compositions of this invention.

1. Properties of Cetosomes and the Aqueous Delivery Matrix

In a specific, but non-limiting aspect of this invention, the microparticles defined herein may comprise one or more active ingredients dispersed within the for delivery matrix. The active ingredients may be for delivery to either humans or animals as a means to manifest a desirable property, activity or purpose.

TABLE 1

| CETOSOME COMPONENT | CARBON ATOMS # | DOUBLE BONDS | MOLEC. WT. (DA) | MELTING POINT (° C.) | HLB VALUE | MINIMUM HLB NEEDED FOR CETOSOME FORMATION |
|---|---|---|---|---|---|---|
| Cetyl Esters | | | | | | |
| Cetyl Octanoate | 24 | 0 | 368.6 | 52-60 | 3.15 | 10 |
| Cetyl Decanoate | 26 | 0 | 396.7 | 40-44 | 2.92 | 10 |

TABLE 1-continued

| CETOSOME COMPONENT | CARBON ATOMS # | DOUBLE BONDS | MOLEC. WT. (DA) | MELTING POINT (° C.) | HLB VALUE | MINIMUM HLB NEEDED FOR CETOSOME FORMATION |
|---|---|---|---|---|---|---|
| Cetyl Laurate | 28 | 0 | 424.74 | 43-45 | 2.73 | 10 |
| Cetyl Isomyristate | 30 | 0 | 452 | 40-46 | 2.57 | 10 |
| Cetyl Myristate | 30 | 0 | 452 | 45-48 | 2.57 | 10 |
| Cetyl Palmitate | 32 | 0 | 480.85 | 54-57° C. | 2.41 | 10 |
| Cetyl Palmitoleate | 32 | 1 | 478.16 | 45-52 | 2.43 | 10 |
| Cetyl Stearate | 34 | 0 | 508.9 | 62-70 | 2.28 | 10 |
| Cetyl Oleate | 34 | 1 | 506.89 | 58-60 | 2.29 | 10 |
| Alcohol components | | | | | | |
| Cetyl Alcohol | 16 | 0 | 242.4 | 49° C. | 3.71 | 15.5 |
| Stearyl Alcohol | 18 | 0 | 270.5 | 59.4-59.8 | 3.33 | 15.5 |

The HLB (hydrophile-lipophile balance) value is defined here as the relative hydrophilicity and hydrophobicity of a molecule. The HLB value is defined as:

HLB=(Formula weight of polar group/formula weight of molecule)×20

In relation to surfactants, surfactants with lower HLB values are more hydrophobic, with greater solubility in oils, while surfactants with higher HLB values are more hydrophilic, with greater solubility in aqueous solutions. Surfactants having an HLB value less than about 10 are considered to be hydrophobic surfactants. Therefore hydrophilic surfactants have HLB values greater than about 10. Combinations of hydrophilic surfactants and hydrophobic surfactants thereof are within the scope of the present invention.

Table 1 provides examples of components used in the formation of cetosome cores. The components in this invention may include but are not limited to those indicated in the table. Components chosen, such as these, have molecular weights with corresponding chain lengths that provide the optimal conformation of the core minimize unfavorable curvature energies. Components with molecular weights ≤500 Da are preferred due to better performance and penetrating agents of those with lower molecular weights. Core components are also chosen with melting points between 40° to 75° C. This allows for thermal dissociation into the oil phase and strong affinity re-association as the temperature is reduced. The HLB values associated with core components have low values, indicative of relative hydrophobicity, also a property required for this invention. The hydrophobicity favors cetosome formation and also favors the stability associated with the nanoparticle. These compounds in Table 1 are associated with high HLB surfactant requirements in order to be solubilized and stabilized within the cetosome.

The partition coefficient, P, is the ratio of solute concentration in binary phases of organic and aqueous solvents. Log P is related to hydrophobicity and usually lipophilicity (since most hydrophobic molecules are also lipophilic) of the nonpolar molecules in an aqueous environment. And the tendency of an aqueous environment to exclude nonpolar molecules is critical to the spontaneous formation of cetosomes. The retention of the hydrophobic components within the cetosome core is in part governed by the partition coefficient of these hydrophobic molecules between the core and the aqueous environment.

Esters are more polar than ethers but less polar than alcohols. They participate in hydrogen bonding as hydrogen-bond acceptors, but cannot act as hydrogen-bond donors, unlike their parent alcohols. This ability to participate in hydrogen bonding confers some water-solubility. The cetylated ester composition of the proposed invention is varied depending on the properties of the active ingredients in the formulation, the properties required for cetosome formation and the desired delivery effects (i.e., systemic delivery, skin delivery, or tissue delivery). Most of the esters utilized in cetosome formation are cetylated esters. However, stearyl esters may also be included in the formation of cetosomes. The cetyl component of the ester also facilitates entry into and through the stratum corneum. However, the alkyl fatty acid or amino ester component composition is variable between formulations depending on the delivery considerations or effects.

1. This component may be of simple alkyl chain length from 8 to 35 carbons, the composition of which may be saturated, mono- to polyunsaturated, or may contain functional groups such as methoxy-, amino- or ring structures.
2. This component may also be branched depending on the desired delivery effects.
3. In some embodiments, where the hydrophilic properties of the drug specify, a cetylated amino ester (such as cetyl arginine and/or cetyl ornithine) is included in the mix of cetylated ester molecules.
4. Different cetylated ester molecule combinations may be used together to provide incorporation of drugs of interest into cetosomes and also to enhance the desired delivery effects. An example would be the combination of cetyl 13-methyl myristate, cetyl linolenate and cetyl isolaurate together to provide increased water solubility and permeation potential for more hydrophilic drugs.
5. Specific but non-limiting examples of cetylated esters that may be used for cetosome formation are: cetyl arginine, cetyl betaine, cetyl 11-cyclohexylundecanoate, cetyl decanoate, cetyl dihomo-γ-linolenate, cetyl dimethicone, cetyl docosapentanoate, cetyl eicosapentanoate, cetyl ethylhexanoate, cetyl isolaurate, cetyl isononanoate, cetyl laurate, cetyl linolenate, cetyl methacrylate, cetyl 13-methyl myristate, cetyl myristoleate, cetyl myristate, cetyl oleate, cetyl ornithine, cetyl palmitate, cetyl palmitoleate, cetylated polyethylenimine, cetyl ricinoleate, cetyl stearate, cetyl stearidonate, stearyl glycyrrhentinate, stearyl stearate and stearyl methacrylate. The cetylated esters or stearyl esters used in combinations of 4 or more for the purposes of this invention.

Two short-chain alcohol components are used in the formation of cetosomes (See Table 1). These are cetyl alcohol and stearyl alcohol. Though cetyl alcohol is a component of the cetosome and is known to form solid crystallization. A review of cetyl alcohol behavior is given in Pasquali, et al. Latin Am J Pharm, 27(8), pp. 839-44 (2008), which is incorporated herein for reference. The behavior of cetyl alcohol shows different behavior due to the composition of the invention which allows for cetosome assembly. While the overall charge of the cetosome is negative at the outer core surface, the short-chain alcohols have a positive polar region as well as the nonpolar alkane chain. Molar ratios of cetyl or stearyl alcohols to cetyl esters of 1:4 to 1:7.4 have shown utility in optimizing cetosome formation and stability. In this manner, both positive and negative charges are interspersed and adjustments of component combinations allow for charge modulation at the core surface into differences in affinity.

The cetyl components are known to have properties conducive for lattice formation.

Polar solvents are required in the present invention to form and maintain the lyotropic phase material. The solvent in the preferred embodiment is prepared to be in equal or nearly equal composition within the particle phase and the continuous (exterior) phase. Some degree of concentration may be found in the mantle region due to charge and surface interactions. Preferably, the polar solvent material in this invention is propylene glycol and the polar lipid material is a combination of cetylated fatty esters (CFE's or also known as cetyl ester waxes). Other polar solvents used instead of or in conjunction with propylene glycol include: dipropylene glycol, ethoxydidlycol, glycerol, ethylene glycol, 1,2,6-hexane triol, 1,2,4-butane triol, propylene glycol ether of methyl glucose or sorbitol, dimethicone copolyol, polyethylene glycol (preferably, PEG 50, PEG 100 and PEG 500), polyvinyl pyrrolidone. For some applications, alcohols (in particular, ethanol, methanol, benzyl alcohol, menthol and isopropanol) may be used as cosolvents. The polar solvent provides hygroscopic and miscible properties that allow solubility for the cetylated esters, which in turn serve to enhance penetration for the permeant. Polar solvents, as well as surfactants, are also used in this invention for penetration enhancement. The behavior of propylene glycol and some of the above solvents as enhancers have been disclosed in U.S. Pat. Nos. 4,973,468, 4,006,218, 3,551,154 and 3,472,931. The design and a preferred embodiment of this invention is the use of enhancers that primarily reduce the diffusional resistance of the stratum corneum. Water, while also a polar solvent, further has use as a phase component that constricts the nanoparticle and maintains restrictive and dispersive effects on these particles.

Figure 1:
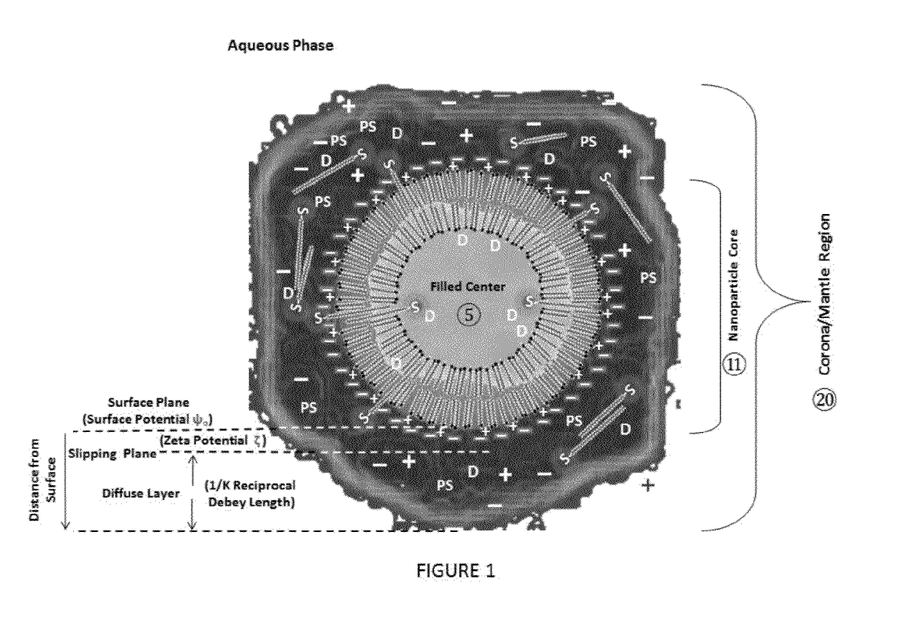

Surfactants are used as amphiphilic, high-HLB components of both core [11] and mantle [21] of the cetosome, as depicted in FIG. 1. The hydrophobic-hydrophilic regions of these medium to long molecules aid in conformational ordering among constituent molecules and in affinity interactions between the phases of the invention system. Examples of surfactants useful in this invention are, but are not limited to, sodium dodecyl sulfate, sodium laureth sulfate, alkyl benzene sulfonate, cetyl trimethyl ammonium bromide, cetyl trimethyl ammonium chloride, cetylpyridinium chloride, benzalkonium chloride, Cremophors (such as Cremophor RH40, Cremophor RH 410, Cremophor RH60, Cermophor EL. Cremophor CO40, Cremophor CO 410 and Cremophor CO60), dodecyl betaine, dodecyl dimethylaminine oxide, cocamidopropyl betaine, nonionic alkyl poly(ethylene oxide), copolymers of poly(ethylene oxide), alkyl polyglucosides, PEG 100 stearate, pluronic F-127, polysorbates (Tween 20, Tween 60 and Tween 80), sodium lauryl sulfate, sodium lauryl sarcosinate, sodium dioctyl sulfosuccinate, sorbitol esters, sorbitan sesquioleate, sucrose cocanoate, sucrose distearate, sucrose dilaurate, sucrose laurate, sucrose palmitate, sucrose polylaurate, sucrose stearate, tragacanth or combinations thereof. Combinations or individual surfactants preferred are those with HLB values greater than 10, but with most preferred values of ≥15. A higher HLB value was discovered to be critical to the present invention due to cetosome core composition and stability observations. The use of high molecular weight surfactant is minimized due to architectural constraints of the nanoparticle. The preferred, but not limiting, concentration of surfactant is 1-10%. Surfactants used in this invention serve as interfacing agents but also serve a dual role as penetration enhancers.

The basic composition of the delivery system containing the cetosome nanoparticles requires a hydrophobic composition phase and a water or aqueous dispersive phase. The hydrophobic phase to aqueous phase ratio in the present invention is preferably from 1:1.4 to 1:2.5. The aqueous phase may have a pH of 4 to 10, and cetosome configuration has been shown to be stable over a wide pH range. The hydrophilic nature of the aqueous phase is critical to the nanoparticle formation and maintenance. Since zeta potential decreases proportionally with increases in ionic strength, the composition is optimized to maintain a high zeta potential. For viscosity and matrix composition within the aqueous phase thickening agents either individually or in combination are incorporated into the formulations. The thickening agents composing the composition base include but are not limited to carbomer polymers (Carbopol 940 NF, Carbopol 934 NF, Carbopol Aqua CC), cellulose esters (such as carboxymethylcellulose), casein, gelatin, glyceryl monostearate, gum Arabic or acacia, hydroxyethyl acrylate, hydroxycellulose, liquid paraffin, polyvinylacetate, polybutylacrylate, polymethylacrylate, polyacrylate-13, polydimethylsiloxane, hydrogels (e.g., high molecular weight polyvinylpyrrolidone, oligomeric polyethylene oxide, or a mixture thereof), liquid paraffin, organogels, and Sodium acryloyldimethyl taurate copolymer, PEF-7 triethylolpropane coconut ether, Sepiplus 400, Sepimax Zen and triethanolamine stearate. The aqueous matrix formed provides for nanoparticle suspension and helps to prevent any potential for coaggulation. The dispersive phase matrix also provides nanostructure that restricts normal particle to particle collisions due to Brownian motion.

Someone skilled in the art will appreciate that other elements and other proportions may be used in the formulations without departing from the desired utility of the formulations defined herein.

2. Architecture of Cetosomes and the Transdermal Delivery System

The dispersion phase (aqueous vehicle phase) of the invention provide suspension stability electrostatic repulsive forces, proper ionic strength. In addition, the dispersion phase contains a suspending matrix that provides an additional steric stabilization to the formed nanoparticles. This combined suspension demonstrates colloid properties and the nanoparticles resist filtration through filters with 0.22 to 0.45 micron pore size. The nanoparticle of this invention is nanostructured to have spherical dimensions that are observable using light microscopy or phase contrast microscopy. The observations best fit microspheres that are lamellar in internal structure with attributes similar to that of anisotropic liquid crystals. The uniformity of microsphere outer morphism and the birefringent nature observed argues for a liquid crystalline structure, since solid crystalline structures tend to be irregular in structure and lacking in the lens-like spherical characteristics found for the cetosomes.

The behavior of these microspheres is unlike that of emulsions in that microscopic examination of cetosomes failed to demonstrate appreciable aggregation into larger spheres after centrifugation (3,500 g for 15 minutes). The cetosomes of this invention are thermodynamically stable. Stability of the cetosome was maintained when temperatures were elevated to 40°±2° C. for 4 or more hours (up to 3 months) and then returned to room temperature. Thermal stress did not result in breakdown of microspheres nor was viscosity decreased due to periods of thermal stress. Real-time stability of nanoparticle and suspension matrix (in an appropriate container at 30°+2° C., 65% humidity) has been observed for finished formulations for up to 18 months of incubation. It is proposed that affinities within the hydrophobic core regions of the cetosomes contribute to the stability observed.

Ternary three-phase mixtures demonstrate potential for nanoparticle polymorphism for with increasing concentrations of surfactant. Like similar molecular types, the components used for cetosome preparation of this invention can be polyphasic, in that different phase configurations can occur depending on the amphiphile composition, composition of liquid and the ampholytic/semi-polar components and temperature. The complete nature of these polymorphisms is beyond the scope of this application. However, the efficacy for transdermal penetration of this invention has been found for the combinations wherein the nanoparticles form spheres. Therefore, attention has been given to alkyl chain lengths and polarity that minimize the degree of other mesomorphic phases. When combinations of mixes were used having HLB values optimized for the formation of cetosomes, the ternary phase mixtures [wherein select cetyl esters (n=8) are at 7% mol, cetyl and stearyl alcohols at 1%, a surfactant A (HLB~18) at 1% and the variable components were surfactant B (HLB 15), water and a polar solvent] demonstrated that conditions necessary for cetosome microsphere formation were when the surfactant B was at 1-20%, polar solvent was at 2-30% and water at 45-70%. Within defined ranges, the cetosome dimensions were found to be adjustable in size through changes in ingredient concentrations while maintaining a spherical particle.

Cetosome construction provides both ionic and nonionic points of attraction. All cetosome particles have two main components: the core [11] and the outer corona or mantle region [20]. These components are indicated in FIG. 1. In addition, within the core of the larger particles there is an outer lamellar structure (that may be composed of multiple layers) with an inner non-solid center [5], in which components introduced as part of the oil phase may be incorporated.

The corona or mantle region [20] is, in part, an accumulation of polar solvent and surfactant molecules that accrue around the core (i.e., form and exterior coating) due to electrostatic interactions between charged groups that arrange at the core surface. This process begins during the cooling phases of manufacture when aqueous and oil phases are mixed. This, too, is an auto-assembly process that continues until the end of manufacture. Also, based on known chemical interactions, surfactants become integrated into the core due to their hydrophobic regions coming into alignment with other hydrophobic core components. The charge regions of the surfactants reach out into the mantle region, participating in the mantle architecture or orientating inward toward the core center, providing a more amphiphilic environment within. Surfactants present natural properties that result in the formation of monolayer of bilayer films around and into the nanoparticles. In this manner they contribute to the "polar-apolar interface" (also termed the "polar-apolar dividing surface"), in which the polar domains at the surface tend to separate from the apolar domains.

The region of the mantle next to the core has an overall negative charge and it is between the core surface plane and a mantle region just above it (the slipping plane) is where the Zeta Potential (Zp) is generated. As the distance from the core surface increases, the mantle composition becomes more diffuse as charge effects decrease. The mantle region is heterogeneous in composition and provides attraction for drug permeants with different affinities. The core, center and mantle can incorporate drug and in doing so, concentrate these active ingredients for improvements in the transdermal delivery process.

Stability of microparticles is a function of the electrical potential at interfaces. The nanoparticles of this invention carry a net negative zeta potential. FIG. 2 shows the zeta potential for cetosomes formed in Composition FC000. This mean Zp reading of −51.6±1.2 (Std Error) mV demonstrates the net effects of the core composition. It is generally agreed that +25 mV or −25 mV or greater is sufficient to stabilize dispersion against flocculation. High aqueous phase conductance, however, results in decreased Zp. In essence the charge is partially screened by the salt counter-ions. This does not appear to affect the nanoparticle stability of this invention. Therefore, for this invention, Zp less than −25 mV is acceptable if the ionic strength of the composition has increased (thereby increasing conductivity) to accommodate better drug stability and skin penetration. For this invention, surfactants with high HLB values (>8) tend to increase particle diameter slightly but also increase trapping of drugs through hydrophilic affinities within the mantle region. The surfactants and solvent molecules within the mantle region also play a role in modulating the Zp. The average range of zeta potentials for all formulations developed to date range from −22 mV to −55 mV. While an inverse relationship was found between zeta potential and conductance, no similar correlation was found between zeta potential and particle size.

The cetosome particles have demonstrated a size range 60 and 850 nm diameter depending on the formulation composition. This size range fits into the definition of a nanostructured particle. A nanostructured particle is defined as a particle composed of nanoscale domains with size orders of nanometers to tens of nanometers ($10\times10^{-9}$ meter). In some developed compositions, two particle sizes were detected with size differences (small to large) between 1:3 to as much as 1:10. FIG. 3 shows the particle size distribution for a Composition CLDC0704 batch. Two peaks were observed with mean diameters of 57.8 and 634.2 nm, respectively. Particles size differences are thought to be the result of different levels of component loading on or within the cetosome. The smaller particles may also contain a lesser liquid or oil center resulting in a particle of lower complexity.

3. Methods for the Manufacture of Compositions Comprising Cetosomes

Some components of the invention may require synthesis. The synthesis of cetyl esters, such as those used for this invention, can be performed by several methods. The following approaches are incorporated herein for reference: Salis, Solinas and Monduzzi, J Mol Catal B-Enzym 21, pp. 167-74 (2003) and Kuo, Chen, Chen, Liu and Shieh, Int J Mol Sci, 13, pp. 11694-704 (2012).

Approaches to manufacture of these compositions are largely those of standard methods, established in the art. Manufacture is designed, however, with the intent to induce auto-assemblies at the molecular level. One aspect of the invention is to combine specific components in phases and then merging these phases in a manner to control molecular organization and integration. The delivery system with resultant nanoparticles is manufactured in 3-4 phases depending on the composition of interest.

An oil or hydrophobe phase (Phase 1) is prepared with components including the cetyl esters and cetyl and stearyl alcohols. Oils or oil-like constituents with HLB values ≥8 can be added to this phase. The phase is heated to a temperature ≥60° C. and mix until all constituents are in liquid form. If drug of interest has hydrophobic properties, it is solubilized in appropriate solvents and/or surfactants but not added to the hydrophobe phase until just prior to mixing of the other phases.

An aqueous-dispersive (hydrophile) phase (Phase 2) is prepared with 30-40% of water used in the composition, preservatives, solvents, surfactants, emulsifiers, humectants and other components which by physical properties would be added to this phase. This is also heated to a temperature ≥60° C. and mix until all constituents are in liquid form.

A gel phase (Phase 3) is prepared with the remaining heated water (at ≥60° C.) used in the composition with the thickeners required for the dispersive phase matrix and additional ingredient required for thickening agent functionality. Buffering agents that achieve the approximate final pH is added and mixed to appropriate consistency.

A fourth phase (Phase 4) is prepared for those components requiring special treatment and those ingredients that may be thermolabile. Some drugs may require addition in this phase. Also ingredients that might interfere with the auto-assembly process are placed in this phase.

Phase 1 is mixed in a measured rate into Phase 2 with torqued, high-shear rotation conducive for preparations of fine emulsions. As mixing progresses the solubilized drugs of interest can be added. With phase mixing complete, Phase 3 is added and mixed to homogeneity. The temperature is then dropped sequentially to the level of 40° C. Rotation torque is also sequentially reduced after the lower temperature is reached. As temperature drops below 50° C., Phase 4 is added. During the temperature reduction, the cetosome components coalesce into nanoparticle cores and mantle components begin interactions with core and initiate generation of the mantle region. All components mix and assemble according to affinities. At this stage, essentially 2 phases exist together, the aqueous dispersion phase and the dispersed phase in which the nanoparticles reside. Upon further cooling, pH and viscosity are adjusted to final specifications and mixing is completed. Timing for each step understood by those skilled in the art. Care must be taken in all steps not to stress components with temperature and times that might bring about degradation. Viscosity, nanoparticle size and properties can be assessed at this final stage.

4. Applications for the Compositions of this Invention

Skin provides a very useful route for delivering local and systemic drugs. This present invention is the discovery of nanoparticles with unique composition for use as therapeutic delivery particles with more effective transdermal penetration. The nanoparticle of this invention can be adapted to carry either lipophilic or hydrophilic drugs, can provide either polar or non-polar regions of affinity, can accommodate wide ranges of pH and drug molecular weights and can be used for transdermal delivery of single drugs or drugs in combination. Efficient and stable encapsulation of compounds into nanoparticles is governed by drug and component solubility and by other physical properties such as rigidity, conformation and molecular weight. There are many substances, which have a strong therapeutic activity but have physical properties that limit their potential for transdermal delivery. In order to increase compatibility between drugs and the core forming components, the cetosome composition can be modified to enhance delivery properties. Since different drugs demonstrate different docking energies, such modifications can also increase the drug loading within the cetosome cores and corona regions. For example, the core components used can be those that are less hydrophobic and the corona can be generated to be more hydrophilic or more positively or negatively charged depending on the charge affinity of a water soluble drug.

Many different applications for use of this invention have been envisioned. Representative examples of pharmaceutical agents include but are not limited to: antidiarrheals, anithypertensives, anticholinergics, calcium channel blockers, antiarrhythmics, antiangina agents, beta-adrenergic blocking agents, adrenergic stimulant, vasodilators, antimigraine prepartions, analgesics and antipyretics, hypnotics and sedatives, antianxiety agents, anti-dandruff agent, neuroleptic and antipsychotic drugs, antidepressants, CNS stimulants, anti-Alzheimer's agents, anti-Parkinson's agents, anticonvulsants, nonsteroidal anti-inflammatory agents, anti-rheumatoid agents, muscle relaxants, agents used in gout and hyperuricermia, ceramides, estrogens, progesterone and other progestagens, antiandrogens, antiestrogens, androgens and anabolic agents, corticosteroids, pituitary hormones and their active derivatives, hypoglycemic agents, thyroid hormones, pituitary inhibitors, ovulation inducers, diuretics, antidiuretics, prostaglandins, antimicrobials, antimalarials, antiparasitics, antiviral agents, antitussives and antihistamines, local or topical anesthetics, protein, peptide, tanning agent, ceramides, neuromuscular blocking agents, smoking cessation agents and allergens for desensitization.

Representative specific examples of therapeutic agents include, but are not limited to: acetaminophen, acetylcholine, acetylcysteine, acyclovir, alpha lipoic acid, ambucaine, amitriptyline hydrochloride, amobarbital, amoxapine, amoxicillin, amphotericin, ampicillin, acetylsalicylic acid, anthralin, ascorbic acid, aspirin, azathioprine, bacitracin, beclomethasone diproionate, benfotiamine, benzethonium chloride, benzocaine, benzodiazepam, betaine, betamethasone, biotin, butacaine, caffeine, codeine, beta-carotine, calciferdiol, calcipotriol, carbamazepine, chloramphenicol, chlorpromazine, cholecalciferol, clarithromycin, clonazepam, cinnarizine, clonidine hydrochloride, cobalamins including cyancobalamin and methylcobalamin, coccidioidin, codeine, coenzyme Q10, colchicine, cyclomethicone, cycloserine, cyclosporine, desipramine, dexamethasone, dexpanthenol, diazepam, diclofenac salts, diethylstilbestrol, difunisal, digitalis, digitoxin, digoxin, dopamine hydrochloride, doxycycline, ephedrine, epinephrine, erythromycin, estradiol, estriol, estrogen, fentanyl, flurouracil, flurazpam, folic acid, gabapentin, gentamicin, griseofulvin, guaifensin, haloperidol, haloprogin, halothane, hydroxyurea, ibuprofen, imipramide and imipramide hydrochloride, Imiquimod, indomethacin, insulin, inulin, ocetamid, isotretenoin, kanamycin sulfate, ketamine, ketoprofen, ketoconazole, levamisole hydrochloride, levodopa, lidocaine, lincomycin hydrochloride, lorazepam, lovastatin, loxapine, mebendazole, melphalan, menadione, mephobarbital, meprednisone, methadone hydrochloride, methyldopa, methotrexate, micronazole, minoxidil, medazepam, nadolol, nalidixic acid, naproxine, neomycin and neomycin sulfate, niacin, nalidixic acid, nitroglycerine, nonoxynol-9, nortriptyline hydrochloride, nystatin, oxacillin sodium, oxamniquine, oxandrolone, oxazepam, oxybenzone, oxybutynin chloride, oxycodone and oxycodone hydrochloride, panthenol, parachlorophenol, phenobarbital, phenophtalein, phenylalanine, phylloquinone, piroctone, piroxicam, pramoxine hydrochloride, prazepam, prednisolone, pregabalin, prilocalne, primidone, procainamide hydrochloride, progesterone, promazine, phenacetin, phenyloin, prednisone, resorcinol, riboflavin, rifampin, salicylamide, salicylic acid, scopolamine, small peptides and oligomers, simethicone, tamoxifen citrate, tetracaine, testosterone, tolazamide, tolbutamide, tolterodine, trentinoin, triacetin, triamcinolone, trientine hydrochloride, triflupromazine, trimethadione, trimethoprim, trioxsalen, tropicamide, trospium, indomethacin, valproic acid, vancomycin hydrochloride, vasopressin, verapramil, vinblastine, vincristine, vitamins, warfarin, piroxicam, haloperidol, and amitriptyline.

Some anti-inflammatory examples of other elements that might be used are: camphor, calamine, capsaicin, eucalyptus oil, lavender oil, menthol, methyl salicylate, rosemary oil and witch hazel.

Compositions of this invention can be administered topically in the form of a cream, gel, lotion, ointment, foam or spray to intact skin, either by the patient or by a medical professional, who applies the required amounts to skin and then uses simple mechanical rubbing into the application site. An alternative approach would be through applying a transdermal patch containing a composition of this invention. A third alternative approach would be through the use of a medical device or an applicator unit designed to hold or apply a composition of this invention and to apply the composition with this device or unit to the application site. A fourth alternative approach would be through the use of a hard or soft matrix gel with dispersive and nanoparticle phases for dispensing using a stick applicator device onto the skin application site. The quantity administered may be with controlled or uncontrolled dose amounts as needed. If the former is required, a dosing of the cream, gel, lotion, foam or spray using measures controlled by weight or volume applied is understood as an extension of this invention. More than one application at a time or multiple applications over an extended time period is understood as a necessary requirement of this invention. Compositions can be prepared in such a way as to delivery drugs for either local or systemic applications. These approaches to application are for illustrative purpose only and do not limit or define the scope of this invention.

EXAMPLES

Example 1

The following as shown in Table 2 are exemplary of compositions, which can be formulated within the scope of this invention. These are for illustrative purpose only and are not intended to define the scope of the invention. All compositions are presented by % weight per volume. The cetylated esters and other components used in developing the nanoparticles of this invention have been described in the "Detailed Description of the Invention."

TABLE 2

Composition Examples for Formulations containing Cetosomes

| | Concentration (% w/v) | | | | | | |
|---|---|---|---|---|---|---|---|
| Ingredient | Formula CLDC-0704 | Formula DPNC-1008 | Formula RDNC-1209 | Formula KKFC-1022 | Formula OFC1030 | Formula PFC1041 | Formula MNA1050 |
| ACTIVE PERMEANTS | | | | | | | |
| Methylcobalamin | — | 0.20 | 0.20 | — | — | — | 0.02 |
| Diclofenac diethylamine & other salts | — | — | 1.16 | — | — | — | — |
| Alpha lipoic acid | — | — | — | — | — | — | 4.00 |
| Ketoprofen HCl | — | — | — | 10.00 | — | — | — |
| Niacinamide | — | — | — | — | — | — | 5.00 |
| Oxybutynin HCl | — | — | — | — | 3.0-10.00 | — | — |
| Pramoxine HCl | — | — | — | — | — | 1.0-2.00 | — |
| CARBOPOL 934NF | — | — | — | — | 0.70 | — | 0.40 |
| CARBOPOL 940 | 0.70 | 0.70 | 0.70 | — | — | — | — |
| CETO &/OR STEARYL ALCOHOL | 2.00 | 2.00 | 2.00 | 1.25 | 2.50 | 4.00 | 2.00 |
| CETYL FATTY ESTERS (Proprietary combinations) | 5.60 | 6.00 | 5.60 | 7.60 | 7.00 | 10.0 | 10.00 |
| CREMOPHORE RH40 | 1.00 | — | 1.00 | — | 1.25 | — | 1.00 |
| ETHOXY DIGLYCOL | — | — | — | 15.0 | — | — | — |
| GLYCERIN | — | — | 2.00 | — | — | 3.00 | 2.00 |
| GLYCERYL MONOSTEARATE | — | — | — | 3.50 | — | — | — |
| HYDROXYPROPYL METHYLCELLULOSE E15 | — | — | — | — | — | 1.00 | — |
| MENTHOL | 1.50 | 5.00 | 1.50 | 3.00 | 1.56 | 5.00 | — |
| ISOPROPYL MYRISTATE | — | — | — | 1.00 | — | 1.00 | — |
| OLIVE OIL | — | — | — | 1.00 | — | — | — |
| PEG 100 | — | — | — | — | — | — | 2.00 |
| PEG 100 STEARATE | — | — | 1.00 | 2.00 | — | — | — |
| PEG 500 | — | — | — | — | — | — | 1.00 |
| POLYSORBATE 80 | — | 2.00 | — | 2.50 | — | 2.00 | 1.00 |
| PROPYLENE GLYCOL | 12.00 | 12.00 | 12.00 | — | 15.00 | 2.00 | 6.00 |
| PRESERVATIVES | 0.22 | 0.22 | 0.22 | 0.22 | 0.28 | 0.78 | 0.80 |
| SEPIPLUS | — | — | — | 1.00 | — | — | — |
| TOCOPHEROL ACETATE | 1.20 | 1.20 | 1.20 | 1.20 | 1.00 | 1.20 | 1.20 |
| BASE EXCIPIENTS | 6.6 | 20.68 | 3.42 | 5.00 | 22.00 | 5.02 | 6.30 |
| FILTERED PURIFIED AQUA | 69.2 | 50.00 | 68.00 | 45.60 | 40-47.10 | 64.0-65.00 | 61.28 |
| pH AGENT | to pH 6.5 | to pH 7.0 | to pH 6.5 | to pH 5.0 | to pH 6.0 | to pH 6.5 | to pH 7.0 |

Composition CLDC0704 is a formulation, in which no drug is added for incorporation into nanoparticles. Composition examples for seven drug, vitamins or antioxidant incorporations are provided in Table 2. The following table provides some characteristics of representative compositions from that table.

TABLE 3

Particle Size, Zeta Potential for Representative Compositions

| Composition | Particle Size (nm diameter)* | | Zeta Potential (mV)* | Conductivity (mS/cm)* |
|---|---|---|---|---|
| | Particle 1 | Particle 2 | | |
| CLDC0704 | 82.6 ± 15.8 | 845.7 ± 114.4 | −49.2 ± 1.2 | 0.016 ± 0.005 |
| DPNC1008 | 95.8 ± 52.5 | 258.0 ± 68.8 | −40.2 ± 2.4 | 0.027 ± 0.002 |
| RDNC1209 | 602.8 ± 4.8 | None detected | −22.3 ± 6.3 | 0.294 ± 0.086 |

*Mean ± SE

Particle size determinations, zeta potentials and conductivities were performed using a Zetasizer NanoZS particle analyzer. Three batches for each composition were analyzed for each evaluation, and each batch was tested in triplicate. Real time stability (25° C., 65% humidity) has been established for each of the above compositions: CLDC0704 (26 months), DPNC1008 (real time and 40° C., 75% humidity stability up to 6 months), and RDNC1209 (18 months). Stability parameters include nanoparticle integrity, analyte concentration, pH and viscosity (no change from baseline >10%). Further studies would be required to establish complete stability limits.

Example 2

Ten volunteers (males and females, 24-35 years of age) were tested to observe bioavailability of diclofenac after application of the RDNC1209 composition. An established commercial product containing 1.16% diclofenac was used as a bioequivalence comparator. The comparator composition (Vv) was an emulsion gel product containing alcohol as one of the penetration agents. Micelle properties of Vv were analyzed using a Zetasizer NanoZS particle analyzer. The emulsion micelles in the Vv comparator have an average diameter of 1.082 microns with a strong zeta potential of −65.4 mV. The comparator conductivity was 0.032 mS·cm. Participants were randomized into 2 groups for topical application. For each treatment, the topical application of 4 grams was applied twice, once at 0 hr and again at 4 hr. Venal blood was drawn six times over a period of 8 hrs using indwelling cannulas. The plasmas were then extracted and analyzed by HPLC using an internal control of ibuprofen. The results were analyzed for $T_{max}$, Cmax, and $AUC_{0-8}$. Bioequivalence was defined using $AUC_{0-8}$ and $C_{max}$ to compare RDNC1209 to the comparator composition.

Results.

No adverse skin reactions were noted during the study period or afterward. The results are presented in Table 4. It was noted that 2 distinct $C_{max}$ peaks were detected for the RDNC1209 composition, associated with the two study applications. The two applications appear to be additive in plasma concentration two peaks. It may be assumed that the two doses were additive to some extent as the second $C_{max}$ is slightly higher and the area under the second peak is greater and the concentration in the plasma ($AUC_{4-8+}$) appears to be greater than that for the first application. Both peaks occurred approximately 2 hrs after each application. Only one peak was observed with the Vv composition; however, it is possible that the kinetics for this product were slower and the $2^{nd}$ peak may appear at some time after 8 hrs.

TABLE 4

Bioavailability/Bioequivalence Study (n = 10)

| | Mean plasma values (Median value) | |
|---|---|---|
| Parameter | RDNC1209 | Vv (Comparator) |
| $T_{max1}$ | 2.3 hr | 2.5 hr |
| $T_{max2}$ | 6.0 hr | None detected |
| $C_{max1}$ | 161.5 ng/ml (115.8) | 84.5 ng/ml (20.6) |
| $C_{max2}$ | 174.2 ng/ml (107.9) | |
| $AUC_{0-8\ hr}$ | 926.6 ng × hr/ml | 427.4 ng × hr/ml |

As noted in Table 4, the comparative kinetic values for RDNC1209 and Vv suggest a greater overall delivery with the RDNC1209 composition. The $C_{max1}$ for RDNC1209 is approximately twice that of Vv, and the same difference is also noted in the $AUC_{0-8\ hr}$. Several published studies of clinical trials have indicated that an effective therapeutic dose would be ~100 ng/ml or greater. In our study, RDNC1209 provided an effective dose by at least 1.5 hrs after application and a therapeutic level was maintained with the two dosing combinations throughout the remainder of the evaluation period (i.e., up to 8 hrs). None of the evaluation times for Vv showed an average plasma concentration for diclofenac of 100 ng/ml or greater.

Conclusion:

These results suggest that the delivery of diclofenac using RDNC1209 was at least equivalent if not superior to that of a commercially available product. It also indicates that RDNC1209 can provide dosing within suggested therapeutic limits, which is indicated in some clinical trials to be ~100 ng/ml or greater. RDNC1209 in this study appeared to have a more effective delivery system than that of Vv.

Example 3

This is also an example for RDNC1209, concerning a clinical experience (Phase 2) study on 100 patients to assess the preliminary safety and potential efficacy of the RDNC1209 composition. This study evaluated the efficacy of the topical formulation as a possible adjunct to various therapies used for treatment of patients with chronic discogenic pain or as a stand-alone treatment. This is an open label study, and the patients were given this treatment option on a voluntary basis.

The candidates for the study were patients (n=100) with chronic discogenic pain that did not respond to conservative treatment. The main criteria for inclusion were: a) the existence of axial low back pain present for 6 months or more and b) disc degeneration or internal disc disruption at a minimum of one level and maximum of two levels, determined by MR imaging and/or positive discography. Patient ages ranged from 22 to 40 yrs., and they were observed to have a mean duration of symptoms of about 24-40 months. Physical function was assessed using the Oswestry Disability Index and measuring the pain with VAS (Visual Analogue Scale) Pain Scale. Patient satisfaction was evaluated using a 0-4 grade scale. Follow-ups were made 1,2 and 3 months after treatment. The RDNC1209 was provided to the applicants in 2 formats: either as a topical cream or as a topical gel stick (aqueous dispersal phase not shown in Table 2).

Results:

Patients were tested randomly over a course of 18 months. At the end of a 2-month treatment, 75% of patients reported a 50% or more reduction in pain, while 85% of the patients reported a reduction of at least 2 points in their VAS values (on a VAS scale of 0-4, 4 being the most painful and 0 being no pain). No side effects from the topical cream were observed in any of the patients. A major finding in the study is that composition formats provided sustained pain relief of several hours after application.

Conclusion:

RDNC1209 had a 75% or better efficacy and was shown to be an alternate, fairly effective and safe method of treatment for discogenic back pain. The particle composition did not adversely affect the patients.

Example 4

Eight volunteers (males and females, 24-35 years of age) were tested to determine ketoprofen absorption bioavailability using the KFC1022 composition. The ketoprofen concentration in the formula was 10% w/v, and only 1.5 grams of the cream (150 mg of ketoprofen) was applied to the skin. This amount was applied twice, once at 0 hr and again at 4 hr. Venal blood was drawn five times over a period of 6 hrs using indwelling cannulas. The plasmas were then extracted and analyzed by HPLC using an internal control of phenacetin (100 ng/ml). The results were analyzed for $T_{max}$, $C_{max}$, and $AUC_{0-8}$. No comparator composition was tested because at this time there are no topical products available commercially that contain 10% ketoprofen. However, there is a published $C_{max}$ value for a topical product under development (designated here as KP10). This value is for a 10% ketoprofen application with a single 100 mg dose kinetics and the $C_{max}$ value is provided for comparison. The data are presented in Table 5.

Results.

The KFC1022 composition provided efficient delivery of ketoprofen transdermally. Cmax for the first application was observed at approximately 2.8 hrs and the concentration in the plasma remained more constant (compared with diclofenac kinetics) giving a fairly constant concentration within the plasma of 50-60 ng/ml. Only 2 topical applications provided at least 5 hrs of concentrations within this concentration range. As with diclofenac individual variability was observed but concentrations in plasma with ketoprofen showed less variability. A second $C_{max}$ was estimated; however, observations beyond 6 hrs were not taken in this study. No adverse reactions were noted in this study.

TABLE 5

Bioavailability Kinetics for Ketoprofen Transdermal Delivery

| | Mean plasma values (range) | |
|---|---|---|
| Parameter | KFC1022 | KP10 (100 mg applied) |
| $T_{max1}$ | 2.8 hr | |
| $T_{max2}$ | 6.0 hr | |

TABLE 5-continued

Bioavailability Kinetics for Ketoprofen Transdermal Delivery

| | Mean plasma values (range) | |
|---|---|---|
| Parameter | KFC1022 | KP10 (100 mg applied) |
| $C_{max}1$ | 67.7 ng/ml (53.6-82.2) | 39.0 ng/ml |
| $C_{max}2$ | 74.0 ng/ml (55.6-92.4) | |
| $AUC_{0-8\,hr}$ | 299.1 ng × hr/ml | |

Conclusion:

KFC1022 effectively delivered ketoprofen through the skin and into systemic circulation, as observed by resulting plasma concentrations. Based on the published information for KP10, the level of ketoprofen delivered may be greater using the KFC1022 composition. Results suggest the efficacy of the present invention as a system to provide efficient transdermal delivery of this NSAID.

Example 5

Urinary incontinence is thought to affect about 15% of the world population with about 17 million of these people residing in the USA. Topical delivery is considered as an potential method for providing an effective dose of anticholinergics in a manner that will reduce undesirable secondary side effects. A pre-clinical feasibility study was performed to determine efficacy of placing these drugs into the nanoparticle delivery system. The OFC1030 composition (in which oxybutynin, a muscarinic receptor antagonist, was incorporated into nanoparticles) was used to test this feasibility and was prepared in the manner described previously herein. Several earlier compositions provided good particle accommodation for oxybutynin; however, it was found with OFC1030 that a preferred nanostructure composition was obtained with propylene glycol at 15%, cetyl and stearyl esters at 2.5%, a select combination of cetyl esters (n=8) at 7% and Cremophore RH 40 (HLB 14-16; a combination of glycerol polyethylene glycol oxystearate, fatty acid glycerol polyglycol esters and glycerol ethoxylate) at 1.25%.

The final composition to be used in the animal studies was evaluated for stability and was found to maintain composition, integrity, pH and analyte concentration for up to 6 months at 40° C., 75% humidity (within a 30 gram fill Lami tube).

Two levels of oxybutynin hydrochloride for use in the study were incorporated into the composition matrix: 5 mg/gm and 0.5 mg/ml. Three rabbits were chosen for each dosing. Animal backs were shaved were shaved 24 hrs prior to application. One gram was applied to the shaved area and rubbed in. This was covered by non-absorbent dressing. One milliliter of blood was collected from a marginal ear vein at baseline, 15 minutes, 1 hr, 6 hrs, 12 hrs and 24 hrs following dosing. Heparin was used as anticoagulant. Extracted samples were analyzed using an LC/MS-MS spectrometer (API 3000) with diazepam as an internal standard. Mobile phase was a 50:40:10 mixture (methanol:acetonitrile: 10 mM ammonium formate). The column used was a Phenomenex, Luna C18, 150×4.6 mm, 5 micron. Temperature for analysis was 30° C. with a flow rate of 1.0 ml/min with splitter with detection using ESI positive ion. Both oxybutynin and N-desethyl-oxybutynin were analyzed. N-desethyl-oxybutynin (DES) is a metabolite of oxybutynin considered to be associated with adverse secondary side effects.

Results.

The pharmacokinetic results are given in Table 6. An efficacy of delivery of the anticholinergic was demonstrated. Delivery was found to be dose dependent with the 5 mg application considered to show a desired feasibility. This dose showed elevated plasma concentrations for 6 hours after application with an acceptable concentration (>2 ng/ml) for most of the 24 hours of observation. As indicated in the table, the 5 mg dose provided drug gradually and systemically, reaching a $C_{max}$ at 6 hours post application. It was also noted that the metabolite N-desethyl-oxybutynin was not detectable during the 24 hour period for either level of dose application. This was considered to be a favorable result for this method of delivery. Therapeutically effective drug levels for humans has been indicated by others to be between 0.5 ng/ml to 3 ng/ml of plasma when administered using a transdermal patch (U.S. Pat. No. 5,411,740 to Lee, Nedberge and Yum, issued May, 1995). No adverse dermal reactions were observed for any of rabbits treated.

TABLE 6

Bioavailability Kinetics for Oxybutynin Transdermal Delivery

| | Mean plasma values | | | |
| --- | --- | --- | --- | --- |
| | Cream, 5 mg/ml | | Cream, 0.5 mg/ml | |
| Parameter | Oxybutynin | DES* | Oxybutyn | DES |
| Cmax (ng/ml) | 9.33 | <0.5 | 0.836 | <0.5 |
| Tmax (hr) | 6 | <0.5 | 12 | <0.5 |
| AUC 0-24 hr (ng × hr/ml) | 21.958 | <0.5 | 2.512 | <0.5 |

*= desethyloxybutynin

Conclusion:

OFC1030 effectively delivered oxybutynin through the skin and into systemic circulation, as observed by resulting plasma concentrations. The composition has since been found to usable with higher concentrations of oxybutynin. Feasibility of formulating using this present invention has also been demonstrated for tolterodine and trospium.

We claim:

1. A composition for transdermal delivery of a bioactive agent comprising:
   a. an aqueous-dispersive phase consisting of water at 40% or more of the delivery composition by weight and supportive base components;
   b. nanoparticles comprising:
      i. 4-20% of delivery composition weight of four or more cetylated or stearyl esters in combinations best suited for the permeation of said active agent through the skin; said cetylated compounds are selected from the group consisting of cetyl arginine, cetyl betaine, cetyl 11-cyclohexylundecanoate, cetyl decanoate, cetyl dihomo-γ-linolenate, cetyl dimethicone, cetyl docosapentanoate, cetyl eicosapentanoate, cetyl ethylhexanoate, cetyl isolaurate, cetyl isononanoate, cetyl laurate, cetyl linolenate, cetyl methacrylate, cetyl 13-methyl myristate, cetyl myristoleate, cetyl myristate, cetyl oleate, cetyl ornithine, cetyl palmitate, cetyl palmitoleate, cetylated polyethylenimine, cetyl ricinoleate, cetyl stearate, cetyl stearidonate, stearyl glycyrrhetinate, stearyl stearate and stearyl methacrylate; and
      ii. cetyl or stearyl alcohols, either singly or in combination, to have a molar ratio to cetyl esters of 1:3 or greater; and
      iii. interfacing agents comprising:
         1. 1-20% of delivery composition weight of one or more surfactants; and
         2. one or more polar solvents present in combined concentrations ranging from 2-30% of delivery composition weight, wherein the solvents are selected from the group consisting of alcohols, dipropylene glycol, ethoxydiglycol, glycerol, ethylene glycol, 1,2,6-hexane triol, 1,2,4-butane triol, propylene glycol ether of methyl glucose or a sorbitol, dimethicone copolyol, a polyethylene glycol, polyvinyl pyrrolidone and propylene glycol, wherein the nanoparticles have a zeta potential ranging either from −20 mV to −100 mV or from +20 mV to +100 mV.

2. The composition of claim 1 wherein said one or more surfactants are selected from the group consisting of sodium dodecyl sulfate, sodium laureth sulfate, alkyl benzene sulfonate, cetyl trimethyl ammonium bromide, cetyl trimethyl ammonium chloride, cetylpyridinium chloride, a cremophor, benzalkonium chloride, dodecyl betaine, dodecyl dimethylaminine oxide, cocamidopropyl betaine, nonionic alkyl poly(ethylene oxide), copolymers of poly(ethylene oxide), alkyl polyglucosides, PEG 100 stearate, pluronic F-127, polysorbate, sodium lauryl sulfate, sodium lauryl sarcosinate, sodium dioctyl sulfosuccinate, sorbitol esters, sorbitan sesquioleate, sucrose cocanoate, sucrose distearate, sucrose dilaurate, sucrose laurate, sucrose palmitate, sucrose polylaurate, sucrose stearate and tragacanth.

3. The composition of claim 1, wherein said delivery composition is in the form of a cream, gel, ointment, foam, lotion, spray, patch, or stick gel.

4. The composition of claim 1, further comprising one more bioactive active agents, wherein the one or more bioactive agents are selected from the group consisting of an anesthetic, antidiarrheal, antioxidant, analgesic, antihypertensive, anticholinergic, antiarrhythmic, beta-adrenergic blocker, adrenergic stimulating agent, vasodialator, antimigraine, antineuropathic pain agent, diuretic, antidiuretic, antimicrobial, antiviral, antipyretic, antipsychotic, antidepressant, anticonvulsant, nonsteroidal anti-inflammatory, anti-rheumatoid agent, steroid replacement agent, corticosteroid, neuromuscular transmission blocker, allergens for desensitization, antidandruff agent, anti-skin cancer agent, antihistaminic, ceramide, protein, peptide, tanning agent or a cosmeceutical compound.

5. The composition of claim 4, wherein the bioactive active agent, alone or in combination, is oxybutynin, tolterodine, trospium, testosterone, estrogen, estradiol, progesterone, corticosteroid or prednisone.

6. The composition of claim 4, wherein the bioactive active agent alone or in combination is selected from the group consisting of amitriptyline, ambucaine, ketamine, nortriptyline, valproate, phenytoin, thiopentone, pentobarbital, propofol, isoflurane, felbamate, lorzapam, midazolam, benzodiazepam, diazepam, lidocaine, clobazam, folinic acid, pyridoxine, gabapentin, oxycodone, pramoxine and pregabalin.

7. The composition of claim 4, wherein the bioactive active agent alone or in combination is diclofenac, ketoprofen, ibuprofen, naproxen, other COX1 or COX2 enzyme inhibitors, a vitamin, methylcobalamin, panthenol, benfotiamine, niacinamide, calcipotriol, catechin, capsaicin or curcumin.

8. The composition of claim 4, wherein the bioactive active agent alone or in combination is a protein based serum, a ceramide, small peptides, an antioxidant, a co-polymer or an elastomer for use in skin firming.

9. The composition of claim 4, wherein the bioactive active agent alone or in combination is one or more soluble pollen allergens for use in allergen immunotherapy.

10. The composition of claim 4, wherein the bioactive active agent alone or in combination is imiquimod, methotrexate, vinblastine, vincristine, or tamoxifen.

11. The composition of claim 1, wherein an amount of the composition is configured to be applied to the skin surface by hand or by the use of an application device, either as a measured or unmeasured dose, and wherein upon application, the composition is configured to improve transdermal absorption of the bioactive agents.

12. Nanoparticles comprising:
    a. 4-20% of delivery composition weight of four or more cetylated or stearyl esters in combinations best suited for the permeation of said active agent through the skin; said cetylated compounds are selected from the group consisting of cetyl arginine, cetyl betaine, cetyl 11-cyclohexylundecanoate, cetyl decanoate, cetyl dihomo-γ-linolenate, cetyl dimethicone, cetyl docosapentanoate, cetyl eicosapentanoate, cetyl ethylhexanoate, cetyl isolaurate, cetyl isononanoate, cetyl laurate, cetyl linolenate, cetyl methacrylate, cetyl 13-methyl myristate, cetyl myristoleate, cetyl myristate, cetyl oleate, cetyl ornithine, cetyl palmitate, cetyl palmitoleate, cetylated polyethylenimine, cetyl ricinoleate, cetyl stearate, cetyl stearidonate, stearyl glycyrrhetinate, stearyl stearate and stearyl methacrylate; and b. cetyl or stearyl alcohols, either singly or in combination, to have a molar ratio to cetyl esters of 1:3 or greater, and c. A combination of interfacing agents derived of the following:

i. 1-20% of delivery composition weight of one or more surfactants; and ii. one or more polar solvents present in combined concentrations ranging from 2-30% of delivery composition weight, wherein the solvents are selected from the group consisting of alcohols, dipropylene glycol, ethoxydiglycol, glycerol, ethylene glycol, 1,2,6-hexane triol, 1,2,4-butane triol, propylene glycol ether of methyl glucose or a sorbitol, dimethicone copolyol, a polyethylene glycol, polyvinyl pyrrolidone and propylene glycol, wherein the active bioactive agent or combination of bioactive agents is incorporated in a suitable combination so as to provide effective transdermal delivery of the agent(s), wherein the nanoparticles have a zeta potential ranging either from −20 mV to −100 mV or from +20 mV to +100 mV.

13. The nanoparticles of claim 12, wherein the shape of the particle is spherical, oval or rod shaped.

14. The nanoparticles of claim 12 having a physical dimension size range between 30 nm to 5 micron in size with a lamellar internal core and an exterior coating comprised in part by interfacing agents.

15. The composition of claim 1, wherein the nanoparticles have a physical dimension size range between 30 nm to 5 microns in size with a lamellar internal core and an exterior coating of a non-lamellar crystalline material.

16. The composition of claim 1, wherein the nanoparticles are created by a method comprising the steps of:

a. preparing a first phase comprising cetyl esters, cetyl alcohols and stearyl alcohols;

b. heating and mixing the first phase until it has liquified;

c. preparing an aqueous second phase comprising:

i. water;

ii. one or more solvents; and iii. one or more surfactants;

d. heating and mixing the second phase until the second phase has liquified;

e. preparing a third phase comprising heated water and thickening agents;

f. creating mixture, comprising the steps of:

i. mixing the first phase into the second phase using torqued, high-shear rotation;

ii. mixing the third phase into the mixture;

iii. mixing one or more solubilized bioactive agents and one or more thermolable agents into the mixture; and iv. sequentially reducing the temperature of the mixture to 40° C., wherein during the temperature reduction, a plurality of nanoparticle components coalesce into a plurality of nanoparticle cores, and a plurality of mantle components interact with the plurality of nanoparticle cores to generate a mantle region for each of the nanoparticles, the mantle region encapsulating the nanoparticle core to form each of the nanoparticles.

17. The nanoparticles of claim 12 created by a method comprising the steps of:

a. preparing a first phase comprising cetyl esters, cetyl alcohols and stearyl alcohols;

b. heating and mixing the first phase until it has liquified;

c. preparing an aqueous second phase comprising:

i. water;

ii. one or more solvents; and iii. one or more surfactants;

d. heating and mixing the second phase until the second phase has liquified;

e. preparing a third phase comprising heated water and thickening agents;

f. creating a mixture, comprising the steps of:

i. mixing the first phase into the second phase using torqued, high-shear rotation;

ii. mixing the third phase into the mixture;

iii. mixing one or more solubilized bioactive agents and one or more thermolable agents into the mixture; and iv. sequentially reducing the temperature of the mixture to 40° C., wherein during the temperature reduction, a plurality of nanoparticle components coalesce into a plurality of nanoparticle cores, and a plurality of mantle components interact with the plurality of nanoparticle cores to generate a mantle region for each of the nanoparticles, the mantle region encapsulating the nanoparticle core to form each of the nanoparticles.

* * * * *